United States Patent [19]

Nakanishi et al.

[11] Patent Number: 5,135,475
[45] Date of Patent: Aug. 4, 1992

[54] APPLICATOR FOR THE USE OF SANITARY GOODS SUCH AS A TAMPON, ETC.

[75] Inventors: Takashi Nakanishi, Utsunomiya; Yasushi Koizumi, Kamagaya; Masayuki Kuboi, Utsunomiya; Yasushi Nakafukushima, Ichigai; Yoshinori Takahashi, Utsunomiya; Tatsuya Yamamoto, Ichigai; Yoshihiro Sakai, Utsunomiya, all of Japan

[73] Assignee: Kao Corporation, Tokyo, Japan

[21] Appl. No.: 747,447

[22] Filed: Aug. 14, 1991

Related U.S. Application Data

[63] Continuation of Ser. No. 391,988, Aug. 10, 1989, abandoned.

[30] Foreign Application Priority Data

| Oct. 13, 1988 | [JP] | Japan | 63-133795[U] |
| Oct. 13, 1988 | [JP] | Japan | 63-257920 |
| Nov. 25, 1988 | [JP] | Japan | 63-297875 |
| Mar. 20, 1989 | [JP] | Japan | 1-32002[U] |
| Mar. 20, 1989 | [JP] | Japan | 1-68710 |

[51] Int. Cl.[5] ............................ A61F 13/20
[52] U.S. Cl. ............................ 604/14; 604/904
[58] Field of Search ............................ 604/11-18, 604/904

[56] References Cited

U.S. PATENT DOCUMENTS

| 2,922,423 | 1/1960 | Richard et al. | 604/14 |
| 3,358,686 | 12/1967 | Asaka | 604/14 |
| 3,753,437 | 8/1973 | Hood et al. | 604/14 |
| 3,765,416 | 10/1973 | Werner et al. | 604/14 X |
| 4,795,422 | 1/1989 | Conner et al. | 604/14 |
| 4,822,332 | 4/1989 | Kajander | 604/16 |

Primary Examiner—C. Fred Rosenbaum
Assistant Examiner—C. Maglione

[57] ABSTRACT

A tampon has an absorbent material and an accommodation barrel for accommodating the absorbent material therein. The accommodation barrel includes an absorbent material accommodating portion for accommodating therein the absorbent material and a clamping portion continuously connected with the absorbent material accommodating portion and has a flexible property. The clamping portion is formed as a large diameter portion which is provided with a ring on an outer circumferential edge thereof.

7 Claims, 11 Drawing Sheets

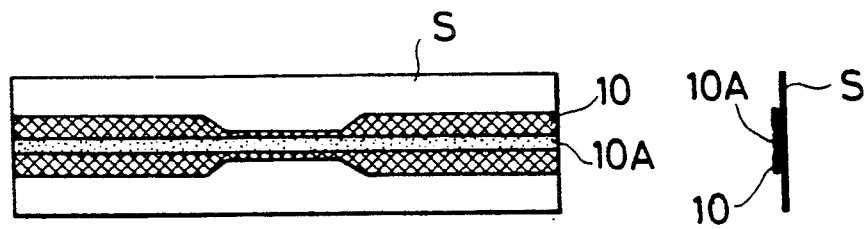
FIG.13    FIG.14
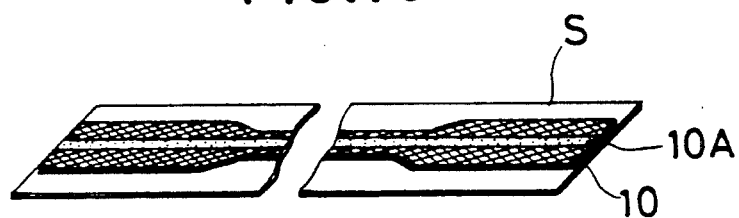
FIG.15
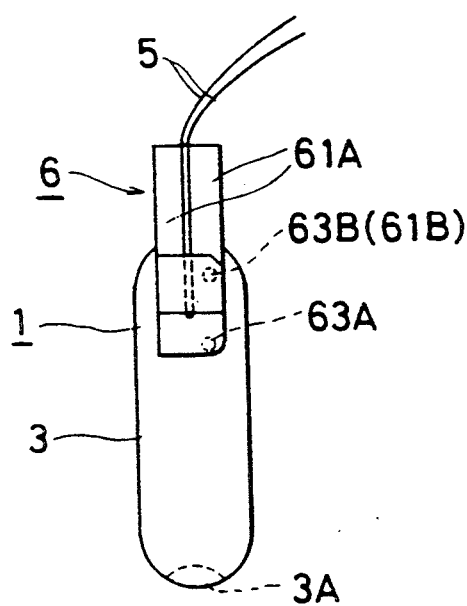
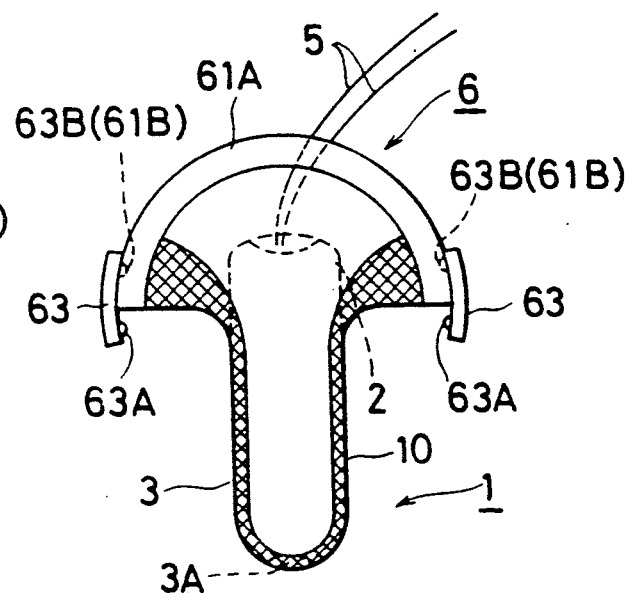
FIG.16    FIG.17

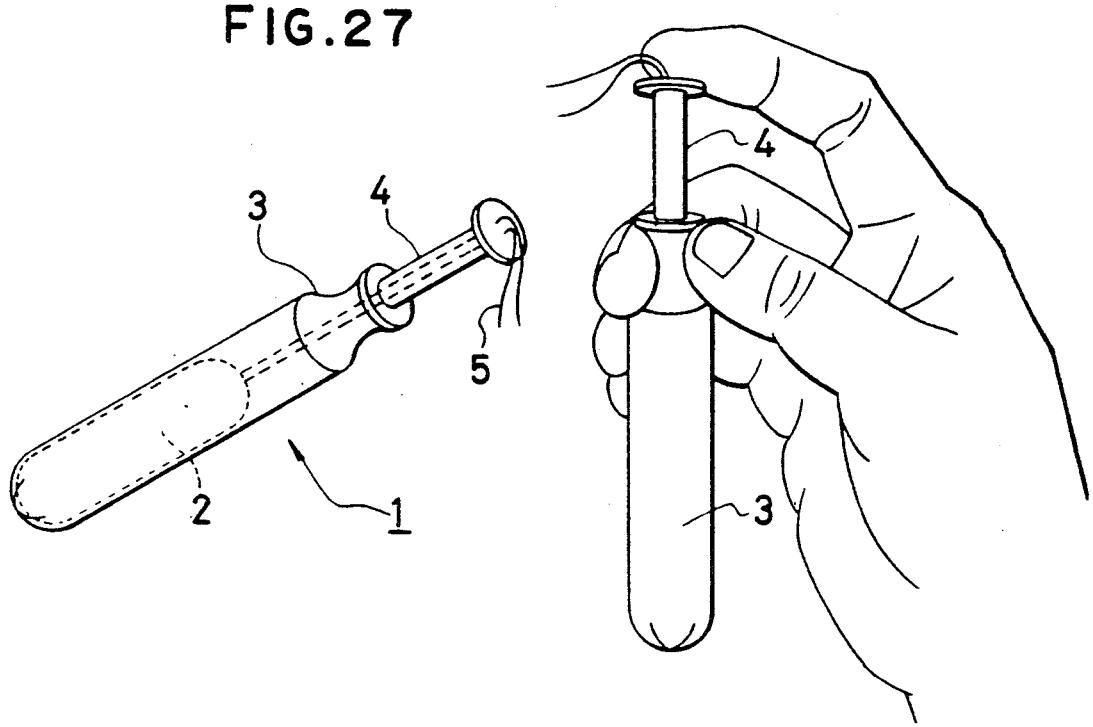
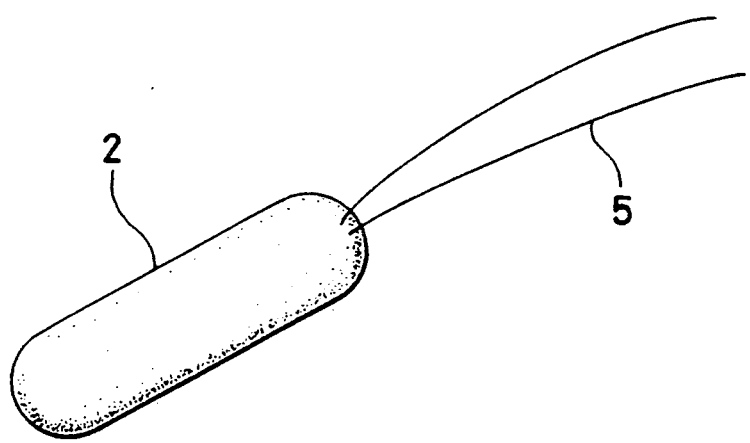

APPLICATOR FOR THE USE OF SANITARY GOODS SUCH AS A TAMPON, ETC.

This application is a continuation of application Ser. No. 07/391,988 filed on Aug. 10, 1989, now abandoned.

BACKGROUND OF THE INVENTION

1. Field of the Invention

This invention relates to a physiological goods for the use of a woman who is in her menstrual period, and more particularly to a physiological tampon which is very sanitary to handle and easy to correctly position when in use. It also relates to an applicator for inserting an absorbent goods, a medical product, or the like into the interior of a human body (hereinafter simply referred to as the "body") such as vagina, rectum or the like, and more particularly to an applicator which is very handy for a woman, who is in her menstrual period, to carry out a sanitary and easy insertion of a tampon into her vagina. It also relates to a method for manufacturing the applicator.

2. Description of the Prior Art

As a representative goods which is to be inserted into the interior of the body, such as an absorbent goods, a medical product or the like, there is a tampon. There are two types of a tampon which is mostly used at present. One is an applicator type and the other is a finger type.

The applicator type tampon has the construction as shown in FIG. 27. An applicator included in this kind of a tampon 1 includes an outer barrel 3 for accommodating therein an absorbent material 2, and an inner barrel 4 which can be inserted into the outer barrel 3. The inner barrel 4 is provided with a tiny hole formed along its axis. This tiny hole serves as an inlet path for pulling out a pull string 5 which is used for pulling out the absorbent material 2 from the interior of the outer barrel 3 to an end portion of an inner barrel 4. The absorbent material 2 used here comprises an absorbent fiber compressed into a cylindrical shape.

Therefore, insertion of the applicator type tampon 1 is carried out in such a manner as shown in FIG. 28. That is, the tampon 1 is clamped with the thumb and the middle finger placed on the outer barrel 3. Then, the index finger is abutted against an end face of the inner barrel. After the outer barrel portion is inserted into and correctly positioned in a predetermined place of the body, the inner barrel 4 is pushed in with the index finger. Then, the absorbent material 2 accommodated in the outer barrel 3 is pushed away from the outer barrel 3 and inserted into a predetermined place of the body. Thereafter, the outer and inner barrels 3 and 4 are withdrawn from the body, thereby to correctly set the tampon in the body.

On the other hand, the finger type tampon 1 does not have an applicator. It merely comprises an absorbent material 2 and a pull-string 5 (see FIG. 29). When in use, the absorbent material 2 is directly inserted into the body.

In general, one of the important reasons why tampons are not spread can be found in the fact that tampons are difficult to insert. It has heretofore been mentioned that a plastic applicator type tampon is the most excellent from a view point of a smooth insertion into the body (FIG. 28).

However, as this type of a tampon is obliged to have an outer diameter the length of which is a sum obtained by adding together the outer diameter of the absorbent material and the thickness of the wall of the applicator, the outer diameter of the tampon becomes long and resistance at the time when the tampon is inserted is increased.

Also, as described in the foregoing, this kind of a tampon is an assembly comprising an inner barrel, an outer barrel and an absorbent material. As the overall length of this tampon is a sum obtained by adding together the length of the outer barrel and the length of the inner barrel, it becomes too long to be held in one hand. Furthermore, it is more desirable to make a tampon as small as possible from a view point that the tampon, i.e., must be disposed after they are used.

In view of the above, a flexible applicator was proposed. However, as this conventional applicator has a uniform expanding property both in the vertical and horizontal directions, the applicator also tends to expand in the vertical direction during an inserting operation. Therefore, much difficulty is encountered when a tampon is inserted into the body.

In a case of molding an applicator which forms a part of the above-mentioned applicator type tampon by using a plane sheet, if a press molding method or vacuum molding method using dies were employed, such methods would basically require a heat control and thus complicated. Moreover, according to the above-mentioned molding methods, it would be the limit that the thickness of the wall of the applicator is 0.2 mm or more and a ratio L/D between the depth L and the diameter D of the applicator is about 2.

On the other hand, in many of applicators for a tampon, the thickness of the wall thereof was generally so thin as 0.2 mm or less and L/D was 2 or more. Therefore, it was difficult to obtain the above-mentioned type of an applicator by means of the conventional molding method which uses dies.

SUMMARY OF THE INVENTION

It is therefore a first object of the present invention to provide a tampon which is capable of overcoming the above-mentioned problems, that is, a tampon in which the outer diameter thereof is similar to the outer diameter of the absorbent material as much as possible and the whole length thereof is about the same to the length of the absorbent material and in addition, when the applicator is disposed, it can be folded into a small size as much as possible.

A second object of the invention is to provide an applicator to be used in a tampon which is compact, easy to position, and sanitary and in which the tampon can be made comparatively compact when packing or carrying with, and also can be folded into a small size as much as possible when disposing.

A third object of the invention is to provide an applicator, in which the outer diameter thereof is similar to the outer diameter of the absorbent material as much as possible and the overall length thereof is about the same to that of the absorbent material, and which is not expanded in the vertical direction even when an absorbent goods, a medical product or the like is inserted into the body, and which is easy to insert and also can be folded into a small size as much as possible when disposing.

A fourth object of the invention is to provide an applicator, in which the outer diameter thereof is similar to the outer diameter of the absorbent material and when an absorbent goods, a medical product or the like is inserted into the body, a frictional force with the finger is reduced so that the overall length of the applicator would not be expanded in the vertical direction, and which is easy to insert and also can be folded into a small size as much as possible when disposing.

A fifth object of the invention is to provide a method for manufacturing an applicator which is 0.2 mm or less in wall thickness and 2 or more in length (L) divided by the diameter (D) very easily and efficiently.

The first object of the present invention can be achieved by providing a tampon comprising an absorbent material and an accommodation barrel for accommodating said absorbent material therein, said accommodation barrel including an absorbent material accommodating portion for accommodating therein said absorbent material and a clamping portion continuously connected with said absorbent material accommodating portion, said clamping portion being formed as a large diameter portion which is gradually increased in diameter as it goes away from one end of the absorbent material accommodating portion, said large diameter portion being provided with a ring. (hereinafter, this invention is referred to as the "first invention", whenever appropriate).

According to a tampon of the first invention, it has no component part corresponding to the inner barrel of the conventional applicator and can be held in one hand. When inserting, the tampon is clamped at the clamping portion with the thumb and the middle finger and is directly inserted into the body. Then, the tampon is retained at the large diameter portion of the applicator, thereby automatically determining the correct position for an inserting end thereof. Then, the absorbent material is pushed into the body with the index finger and thereafter, the index finger is withdrawn. The accommodation barrel is also inserted into and withdrawn from the body in a state where the accommodation barrel is intimately contacted with the index finger. When the index finger is further withdrawn from the body by holding the ring with the other hand, the accommodation barrel is turned inside out with the dirty outer surface of the accommodation barrel turned inside thereof and the clean inner surface outside. As the clean inner surface is turned outside, the accommodating barrel can directly be folded into a small size and disposed.

The second object of the present invention can be achieved by providing an applicator of a tampon (this applicator is a part of the tampon and thus integral with the tampon here) including an accommodation barrel for accommodating therein an absorbent material and a clamping portion continuously connected with said accommodation barrel, said clamping portion being formed of a plurality of framework elements which are adapted to form a framework and foldable. (hereinafter, this invention is referred to as the "second invention", whenever appropriate).

According to an applicator of the second invention, it has no component part corresponding to the inner barrel like in the case of the first invention where the applicator forms a part of the tampon. In addition, the framework can be folded so that the tampon would be compact to carry with.

The third object of the present invention can be achieved by providing an applicator including an accommodating portion for accommodating therein a goods such as an absorbent goods, a medical product or the like which is inserted into the body, and a clamping portion continuously connected with an opening portion of said accommodating portion, said accommodating portion being formed of a flexible structure which has an expanding property able to be expanded in the radial direction, said clamping portion being formed of a framework having sufficient rigidity for holding the opening portion of said accommodating portion. (hereinafter, this invention is referred to as the "third invention", whenever appropriate).

According to an applicator of the third invention, the tampon, when inserting, is clamped at the clamping portion with the thumb and the middle finger and is directly inserted into the body. Then, the tampon is retained at the large diameter portion of the applicator, thereby automatically determining the correct position for an inserting end of the applicator. As the accommodating portion is flexible and small in resistance, an easy insertion can be obtained. When the index finger is withdrawn after the absorbent goods, the medical product or the like is inserted into the body with the index finger, the accommodating portion is inserted into and withdrawn from the body in a state where the accommodating portion is intimately contacted with the index finger pressing the accommodating portion. When the index finger is further withdrawn by holding the framework with the other hand, the accommodation barrel is turned inside out with the dirty outer surface of the accommodating barrel turned inside thereof and the clean inner surface outside. As the clean inner surface is turned outside, the accommodation barrel can directly be folded into a small size and disposed.

And the third object of the present invention can favorably be achieved by providing an applicator in which, in the applicator of the above-mentioned third invention, the flexible structure is formed of a sheet or a fibrous structure of an anisotropic strong expanding property which has a different strong expanding property in the vertical and horizontal axial directions respectively, said accommodating portion being formed of said flexible structure as such that the less expanding vertical axial direction of said flexible structure is served as the longitudinal direction, while the more expanding horizontal axial direction thereof is served as the radial direction.

Also, the third object of the present invention can favorably be achieved by providing an applicator, wherein said flexible structure is formed of an unburned sheet of a tetrafluoroethylene resin of an anisotropic strong expanding property which has a different strong expanding property in the vertical and horizontal axial directions respectively, said accommodating portion being seamless molded of said unburned sheet of a tetrafluoroethylene resin as such that the less expanding vertical axial direction of said unburned sheet is served as the longitudinal direction, while the more expanding horizontal axial direction thereof is served as the radial direction.

According to an applicator, in which, in the applicator of the third invention, the above-mentioned one is used as the above-mentioned flexible structure and the above-mentioned accommodating portion is formed in the same manner as described above, the clamping portion is clamped with the thumb and the middle finger when inserting. When the applicator is then directly inserted into the body, it is retained at the large diameter portion, thereby automatically determining the correct position for the inserting end of the applicator. As the accommodating portion is flexible and small in resistance and is expanded only in the vertical direction instead of being expanded in the horizontal direction, an easy insertion can be obtained. When the index finger is withdrawn after the absorbent goods, the medical product or the like is inserted into the body, the accommodating portion is inserted into and withdrawn from the body in a state where the accommodating portion is intimately contacted with the index finger pressing the accommodating protion. When the index finger is further withdrawn by holding the framework with the other hand, the accommodation barrel is turned inside out with the dirty outer surface of the accommodating barrel turned inside thereof and the clean inner surface outside. As the clean inner surface is turned outside, the accommodation barrel can directly be folded into a small size and disposed.

And, the third object of the present invention can favorably be achieved by providing an applicator in which, in the applicator of the above-mentioned third invention, the flexible structure is formed of a sheet or a fibrous structure of an anisotropic strong expanding property which has a different strong expanding property in the vertical and horizontal axial directions respectively, said accommodating portion being formed of said flexible structure as such that the less expanding vertical axial direction of said flexible structure is served as the longitudinal direction, while the more expanding horizontal axial direction thereof is served as the radial direction.

Also, the third object of the present invention can favorably achieved by providing an applicator, wherein said flexible structure is formed of an unburned sheet of a tetrafluoroethylene resin of an anisotropic strong expanding property which has a different strong expanding property in the vertical and horizontal axial directions respectively, said accommodating portion being seamless molded of said unburned sheet of a tetrafluoroethylene resin.

The fourth object of the present invention can be achieved by providing an applicator, wherein at least a part of an inner surface of said flexible structure is formed of a sheet having an substantially irregular surface. (hereinafter, this invention is referred to as the "fourth invention" whenever appropriate).

According to the applicator of the fourth invention, when the absorbent material is inserted into the body with the index finger, the friction with the index finger is reduced. Therefore, the absorbent goods, the medical product or the like can smoothly be pushed away from the accommodating portion.

The fifth object of the present invention can be achieved by providing a method for manufacturing an applicator which includes an accommodating portion for accommodating therein a goods such as an absorbent goods, a medical product or the like which is inserted into the body, and a clamping portion continuously connected with an opening portion of said accommodating portion, said accommodating portion being formed of a flexible structure which has an expanding property able to be expanded in the radial direction, said clamping portion being formed of a framework having sufficient rigidity for holding the opening portion of said accommodating portion, said method comprising the steps of fixing said flexible structure, which is not substantially expansible in the vertical axial direction and is expansible in the horizontal axial direction, to substantially four corners thereof, and plastic deforming said flexible structure by applying a concentrated load onto a central portion thereof. (hereinafter, this invention is referred to as the "fifth invention", whenever appropriate).

According to the method for manufacturing an applicator of the fifth invention, the flexible structure or sheet, which is not substantially expansible in the vertical axial direction and is expansible in the horizontal axial direction, is fixed to the four corners, and thereafter, the central portion is applied with a concentrated load. As a result, the flexible structure or sheet can be plastic deformed to be formed as the accommodating portion of the applicator.

BRIEF DESCRIPTION OF THE DRAWINGS

FIGS. 8, 9 and 10 are prespectives respectively showing the operation when the tampon of FIG. 5 is inserted, wherein FIG. 8 is a perspective view of a clamping state of the tampons, FIG. 9 is a perspective view showing a state when the tampon is inserted, and FIG. 10 is a perspective view showing a state where only the tampon is withdrawn and turned inside out;

FIGS. 13, 14 and 15 are views respectively showing a sheet forming the applicator, wherein FIG. 13 is a plan view thereof, FIG. 14 is a sectional view thereof, and FIG. 15 is a perspective view showing an exploded state of a central portion thereof;

FIG. 16 is a side view showing a folded state of the tampon of FIG. 11;

FIG. 17 is a front view thereof;

FIGS. 19 and 20 are schematic views showing the sequence of the steps of one mode of the method for manufacturing an applicator of the fifth invention, in which FIG. 19 is a perspective view showing a state immediate before a concentrated load is applied to a sheet, FIG. 20 is a prespective view showing the moment when a barrel-like product is formed by means of concentrated load;

FIGS. 23, 24, 25 and 26 are schematic views for explaining a state wherein the sheet is changed by means of application of the concentrated load, in which FIG. 23 is a plan view showing the sheet before molding by way of analytical method, FIG. 24 is a plan view showing the sheet after molding wherein the sheet is partially changed due to expansion by way of analytical method, FIG. 25 is a side view of FIG. 24, and FIG. 26 is a front view showing a part of FIG. 25;

FIG. 27 is a perspective view showing the conventional applicator type tampon;

FIG. 28 is a perspective view showing a using state of the conventional applicator type tampon; and FIG. 29 is a perspective view showing a finger type tampon which has no applicator.

DETAILED DESCRIPTION OF THE PREFERRED EMBODIMENT

Figure 1:
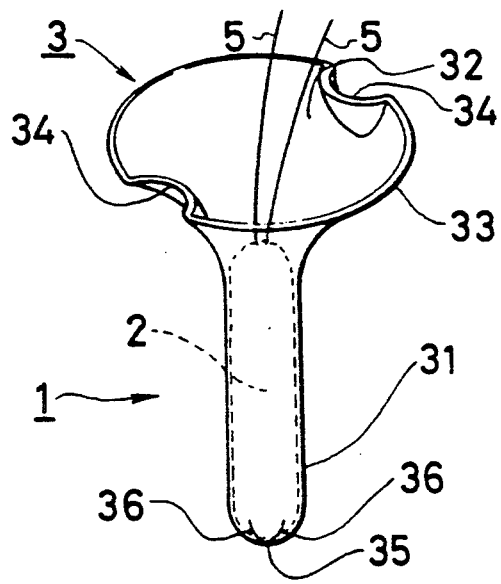
FIG. 1 is a perspective view showing one embodiment of an applicator type tampon of the first invention.

The first invention will be described hereunder with reference to the embodiment shown in FIGS. 1 through 4.

An applicator type tampon 1 according to one embodiment of the first invention comprises an absorbent material 2 and an accommodation barrel 3 for accommodating therein the absorbent material 2 and acting as an applicator. The absorbent material 2 is formed of the same material to that of the conventional one.

The accommodation barrel 3 comprises an absorbent material accommodating portion 31 for accommodating therein the absorbent material 2 which is formed in a generally cylindrical shape, and a large diameter portion 32, the diameter of which is gradually enlarged as it goes away from an opening portion of the absorbent material accommodating portion 31. The large diameter portion 32 is formed at an external circumferential edge thereof with clamping portions 34, 34 opposite with each other. Each of the clamping portions 34, 34 is curved inwardly toward the center so that the finger would easily be abutted therewith. On the other hand, the accommodation barrel 3 is gradually reduced in diameter as it goes toward the tip and is provided with a plurality of perforations 36 formed in the axial direction toward the large diameter portion 32 from a reduced diameter end portion 35 which is closed up. Owing to the foregoing arrangement, when the absorbent material 2 is pushed into the body from the side of the large diameter portion 32, the plurality of perforations are broken by the pushing force thereby to facilitate an easy insertion of the absorbent material 2. Such constructed accommodation barrel 3 is formed of an expansible flexible sheet or film (hereinafter, basically represented by the "sheet"). As the accommodation barrel 3 is formed of the flexible sheet, the outer diameter of the tampon 1 can be formed so thin that it very much resembles to the outer diameter of the absorbent material 2. Also, the flexible sheet used in this embodiment is preferably formed of fibers which prohibit the passage of menstruous blood. As the cylindrical absorbent material 2 is sometimes larger than the index finger, the accommodation barrel 3 for accommodating therein the absorbent material 2 is usually formed of a material which can be expanded in the radial direction when the absorbent material 2 is pushed in. As such a material as mentioned is required, as a material to be used, there are, for example, waved paper class, resin laminated paper, nonwoven fabric (particularly, hydrophobic nonwoven fabric), expansible film (particularly, water soluble film), etc. They are preferably easy to fold in view of packing.

That is, the diameter of such accommodation barrel 3 is required to be expanded one to three times larger than the diameter of the absorbent material 2. For this purpose, there are the following methods.

①  Method for using a sheet expansible in the radial direction.

②  Method for expansion from a folded state.

③  Method for expansion from a narrowed state.

Figure 2:
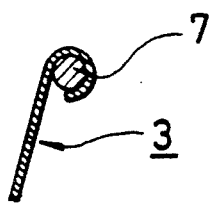
FIG. 2 is a sectional view showing a clamping portion of the tampon of this embodiment.

Also, the large diameter portion 32 is attached at the external circumferential edge 33 with a ring 7 and a part thereof is formed with the clamping portions 34, 34 (see FIG. 2). The ring 7 is clamped with the thumb and the middle finger when the accommodation barrel 3 is inserted into the body. The clamping strength is preferably 10 g to 500 g, and particularly preferably 50 to 150 g.

The ring 7 acts as a positioning stopper when the accommodation barrel 3 is inserted into the body. The ring 7 is required to have a stop bearing force of 10 g to 500 g, particularly preferably 50 to 200 g so as to be able to bear an extruding load of the absorbent material 2 into the body.

From the above-mentioned view point, the outer diameter of the ring 7 is preferably 20 to 50 mm. In the case that the material of the ring 7 is selected from the group of water soluble materials, the ring 7 can be flowed into water after used. As a material having such a property as mentioned, there are, for examples, twisted-paper string rod, water soluble hollow resin rod, etc.

Figure 3:
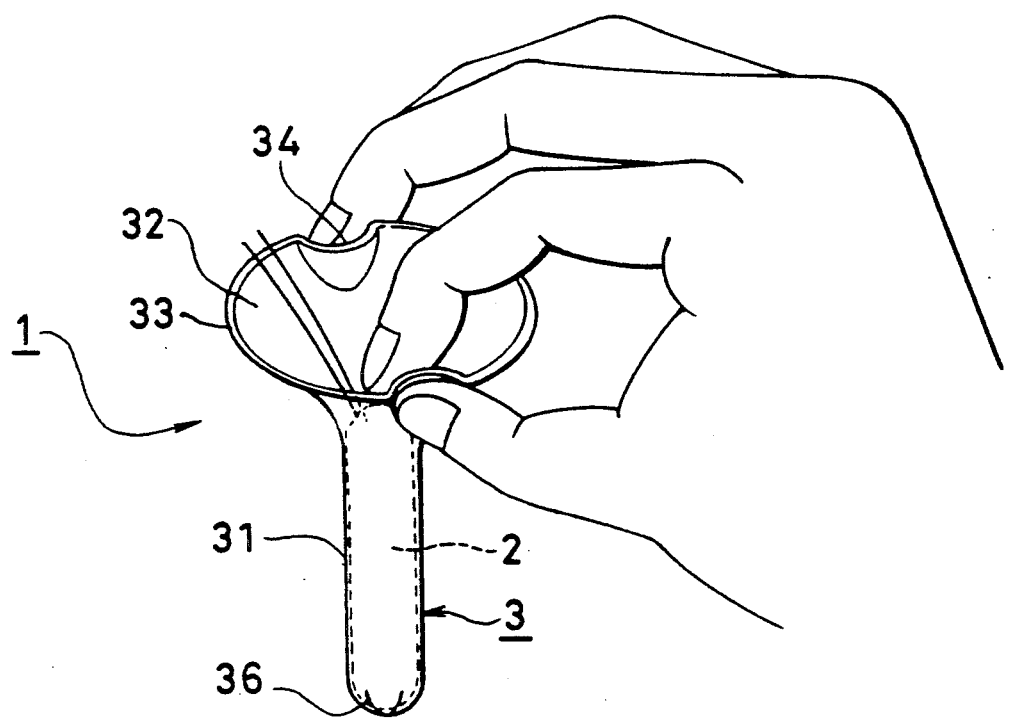
FIG. 3 is a perspective view showing the clamping state when the tampon of this embodiment is inserted.

The tampon 1 of this embodiment is used in the following steps. First, as shown in FIG. 3, the clamping portions 34, 34 of the accommodation barrel 3 is clamped with the thumb and the middle finger and then, while pressing the absorbent material 2 with the index finger, the accommodation barrel 3 is inserted into the body. At this time, as the three fingers are placed near with respect to each other at the tampon 1, a possible adverse affection due to rotation of the wrist is small and a fine adjustment can be effected. Therefore, the position of the index finger for pushing the absorbent material 2 can be finely adjusted in order to delicately change the advancing direction. Therefore, the tampon 1 can be inserted into the body through extremely easy and smooth operation. Moreover, as it is the large diameter portion which is clamped with the fingers, it can be much more easily clamped than in the case where a small diameter portion is clamped.

And, when the accommodation barrel 3 has been inserted into a correct position in the body, it is required merely to remove the thumb and the middle finger and simply to push the absorbent material 2 with the index finger alone. Therefore, adjustment with respect to the direction for the pushing force is very easy.

When the insertion is over, the index finger still inserted into the accommodation barrel 3 is withdrawn. At this time, the index finger can be removed as such that the index finger is in an intimate contact with the inner wall of the accommodation barrel 3. Therefore, there is no sense of unbelongingness. Moreover, the accommodation barrel 3, which follows to the index finger, can be further withdrawn by holding the ring 7 with the other hand. At this time, as the accommodation barrel 3 surrounding the index finger is turned inside out. Therefore, the dirty part of the accommodation barrel 3 is not conspicuous and sanitary. Therefore, it can directly be disposed. Also, by using a water soluble film, it can be flowed into water. Therefore, disposal of the accommodation barrel 3 is easy and convenient.

Figure 4:
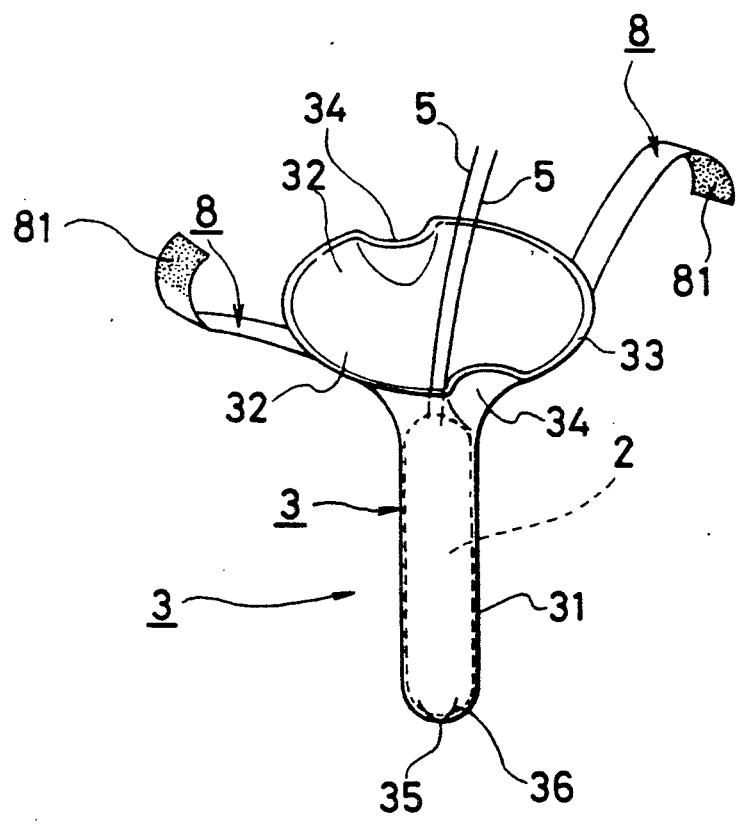
FIG. 4 is a view corresponding to FIG. 1 but showing another embodiment of the first invention.

FIG. 4 is a view showing an applicator type tampon 1 of another embodiment of the first invention. The tampon 1 of this embodiment is different from the tampon 1 of the preceding embodiment only in the respect that a pair of adhesive tapes 8 are attached to a large diameter portion 32 and all the remaining construction is the same to that of the tampon 1 of the preceding embodiment. In order to use the tampon 1 of this embodiment, an adhesive portion 81 of the adhesive tape 8 is attached to a part of the body first and then, the tampon 1 is inserted into the body. By this, the tampon 1 can more easily be inserted into the body. Moreover, the tampon 1 of this embodiment can expect the same function and effect as that of the preceding embodiment.

In the above-mentioned embodiments, the large diameter portion 32 is formed as such that it is gradually enlarged as it goes away from the absorbent material accommodating portion 31. However, the present invention is not limited to this. For example, the tampon may be designed as such that an opening portion of the absorbent material accommodating portion 31 is provided with a large diameter portion 32 which is formed like a flange and is further attached at an external circumferential edge thereof with a ring 7, thereby to form the clamping portions 34, 34 with the same favorable function and effect.

The second invention will now be described with reference to the embodiments shown in FIGS. 5 through 10.

Figure 5:
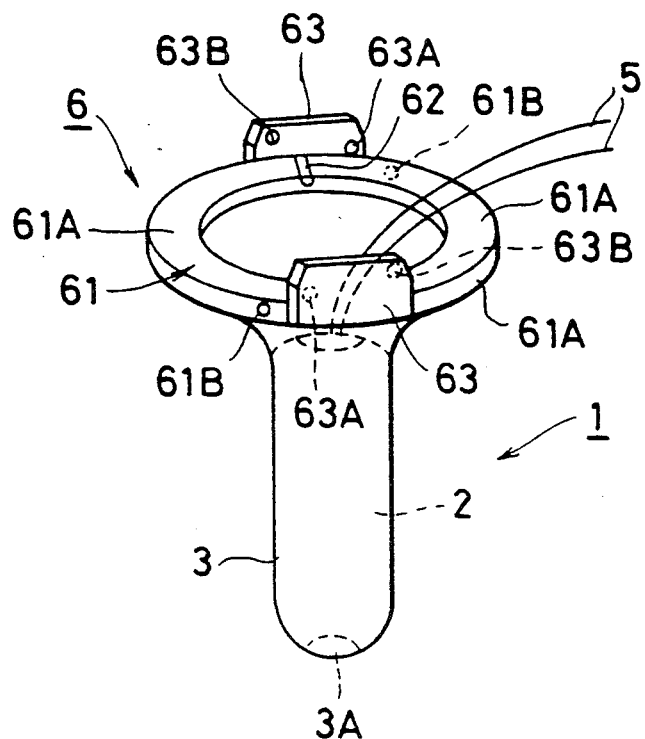
FIG. 5 is an overall perspective view showing one embodiment of the applicator of the tampon of the second invention and one embodiment, in which the applicator of the third invention is applied to the tampon respectively.

An applicator type tampon 1 of one embodiment of the second invention, as shown in FIG. 5, comprises an accommodating portion 3 for accommodating an absorbent material 2, and a clamping portion 6 continuously formed with the accommodating portion 3.

The clamping portion 6 acts as a stopper when the tampon 1 is inserted. The clamping portion 6 is formed with a circular framework 61 and includes a pair of foldable framework elements 61A, 61A. Each of the framework elements 61A, 61A exhibits a semicircular shape which is formed by bisecting the framework 61 with reference to the center thereof. The framework elements 61A, 61A are foldably connected with each other, as mentioned above, through hinges 62, 62 each of which is made of a thin resin film.

In view of the property of a tampon, the framework 61 is preferably 20 to 50 mm in the outer diameter.

Figure 6:
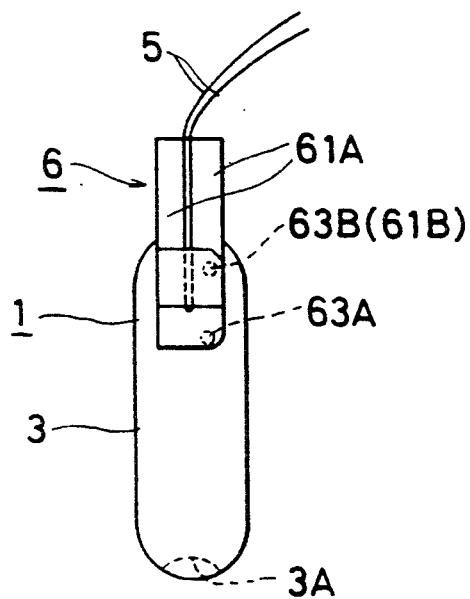
FIG. 6 is a side view showing a folded state of the tampon of FIG. 5.
Figure 7:
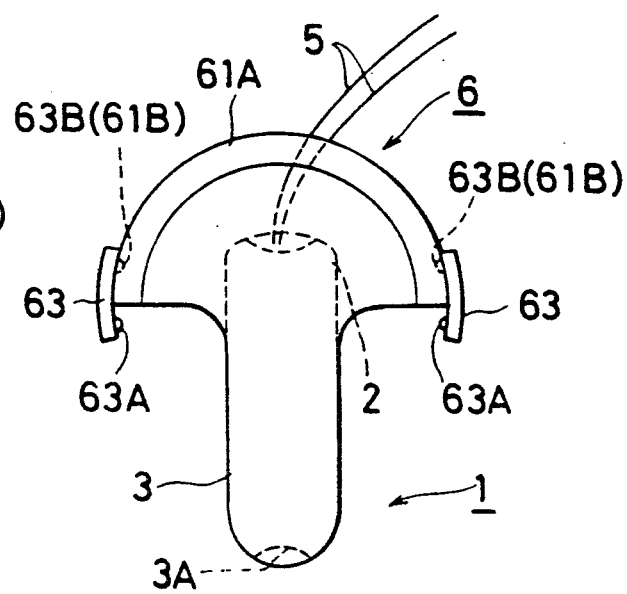
FIG. 7 is a front view thereof.

Also, each of the framework elements 61A, 61A is provided at an outer peripheral surface of a connecting portion thereof with a rectangular clamping plate 63 which is integral with any one of the framework elements 61A, 61A. And, the framework elements 61A, 61A can be folded in a purse-shape through hinges 62, 62 as shown in FIGS. 6 and 7. This feature is advantageous when packing and carrying. More specifically, the clamping plates 63, 63 as shown in FIG. 5, are formed in such a manner as to project from the circular framework 61. The length of the projecting part of each of the clamping plates 63, 63 is the generally same to the thickness of the framework 61. Each of the clamping plates 63A, 63A is provided at its side edges in the projecting direction from each of the framework elements 61A, 61A with a pair of semispherical knobs 63A, 63B diagonally arranged with respect to each other. The knob 63A which occupies a lower position horizontally retains one of the framework element 61A with respect to the other framework element 61A so as to hold the circular framework 61 when is use, while the knob 63B which occupies a higher position is engaged in a recessed portion 61B formed in the outer peripheral surface of the framework element 61A which is at a far side when the framework elements 61A, 61A are folded, so that the framework elements 61A, 61A can be held in a compact size as shown in FIGS. 6 and 7.

Also, the accommodating portion 3 has a hole 3A which is gradually reduced in diameter as it goes toward the tip. The hole 3A is designed as such that the hole 3A is expanded and opened up when the absorbent material 2 of the tampon 1 is pushed away from the accommodating portion 3.

A material forming the accommodating portion 3 is preferably a synthetic resin which can be expansion molded. The synthetic resin is more preferably water soluble. When the material is subjected to the expansion molding, a part of the material, which should not be expansion molded, is pressed and fixed, and the remaining part of the material, which should be expansion molded, is made free and expanded. As a result, there can be obtained an accommodating portion which is partly contracted and is gradually enlarged in diameter in the radial direction at the root portion as shown in FIG. 5.

As such expansible synthetic resin, there can be listed, for example, a polytetrafluoroethylene film. This polytetrafluoroethylene film, when its film thickness is 60 μm, exhibits the following values of physical properties.
① Tension strength in the vertical direction of the film: 1200 g/mm², expanding power: 200%
② Tension strength in the horizontal direction of the film: 100 g/mm², expanding power: 800%

As a material used for forming the clamping portion 6, it is only required to have a strength enough to bear a extruding strength (about 1500 g max.) when the absorbent material 2 is inserted into the body, as the clamping portion 6 has the role for acting as a stopper. As such material, there can be listed a thermoplastic resin such as, for example, polyethylene, polypropylene, etc.

The mode of actual use of the tampon to which the applicator of the above-mentioned embodiment will be described next.

Figure 8:
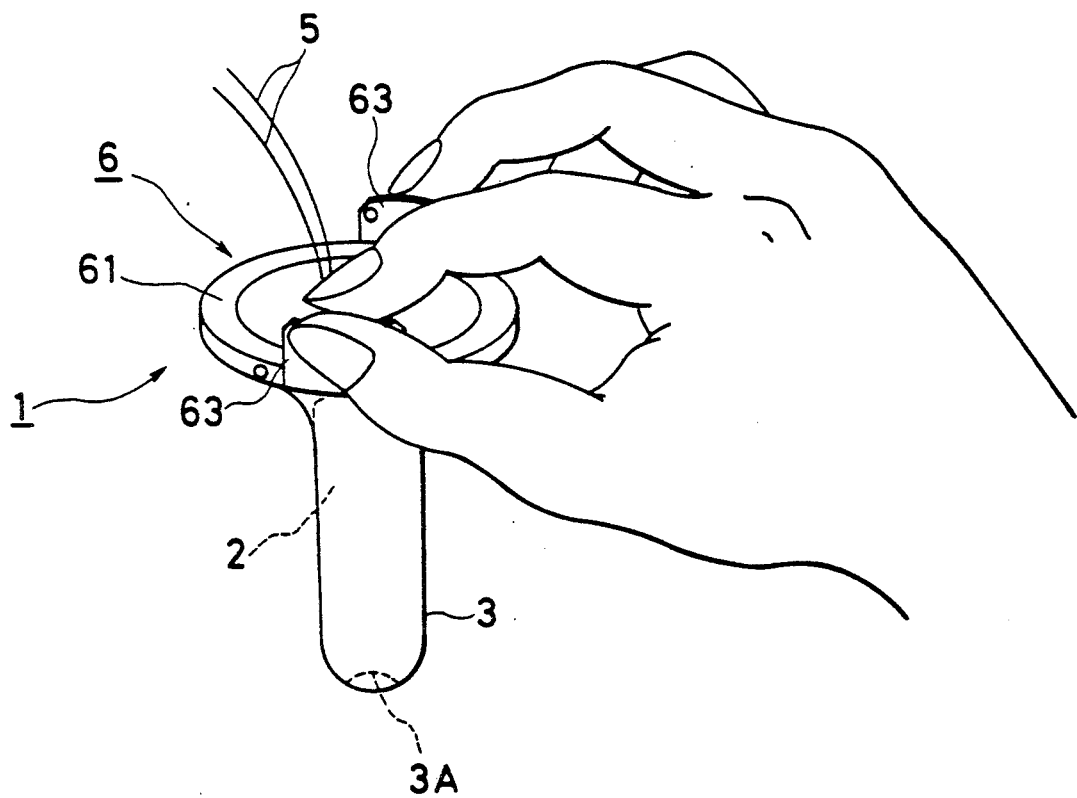
Figure 9:
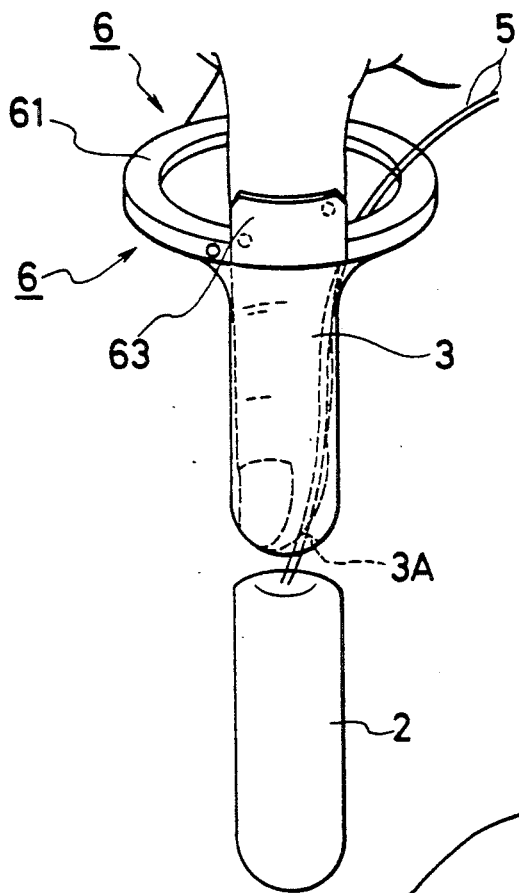
Figure 10:
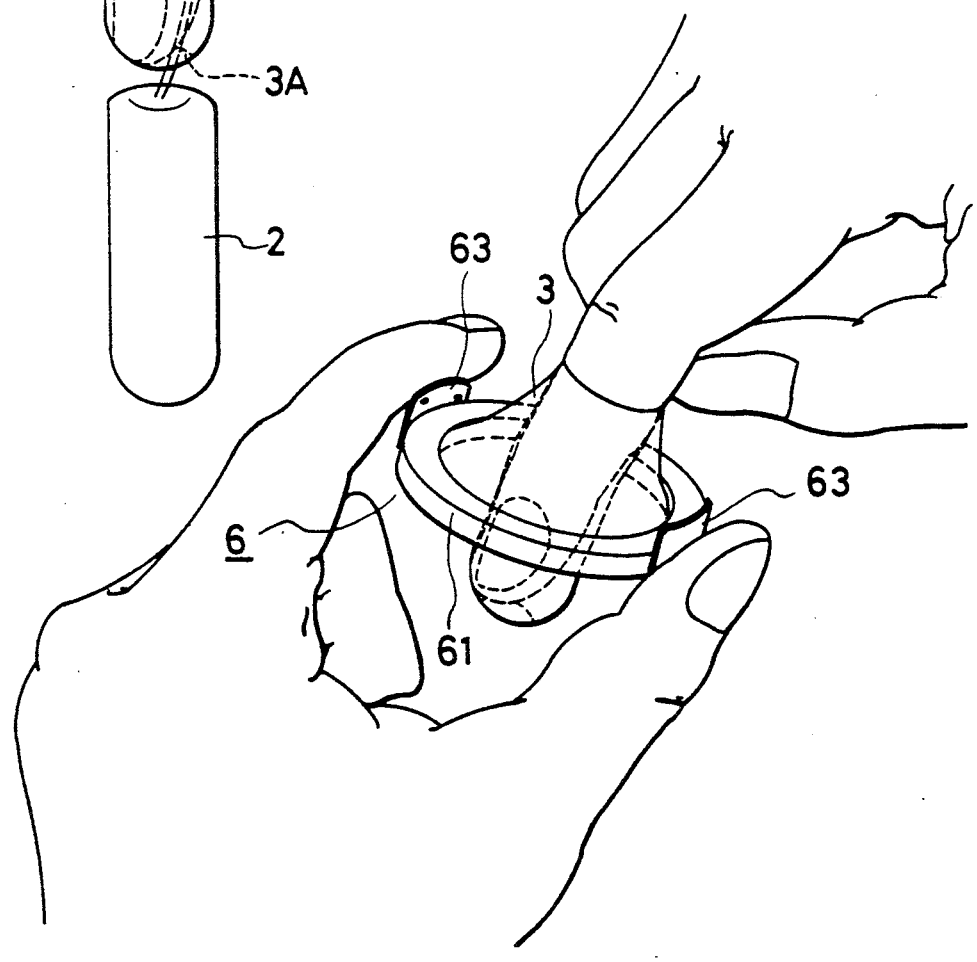

First, as shown in FIGS. 6 and 7, the framework elements 61A, 61A of the tampon 1, which are folded like a purse, are opened to form a circular framework 61 as shown in FIG. 5. Then, as shown in FIG. 8, the clamping plates 63, 63 of the accommodating portion 3 is clamped with the thumb and the middle finger and, while pressing the accommodating body 2 with the index finger, the accommodating portion 3 is inserted into the body as shown in FIG. 9. At this time, as the three fingers clamping the tampon 1 are close to each other, adverse affection due to rotation of the wrist is minor and a fine adjustment in the inserting direction can be obtained. By slightly changing the position of the index finger for pushing away the absorbent material 2, the inserting direction can delicately be changed. Therefore, the tampon 1 can correctly be positioned with ease, and it can much more easily be inserted into the body when compared with the conventional tampon. In addition, as it is the framework 61 which is clamped with the fingers, the tampon 1 can much more easily be clamped when compared with the conventional tampon in which the fingers clamp the applicator having a small diameter.

Also, the absorbent material 2 can be inserted in the body merely by pushing away the absorbent material 2 with only the index finger after the tampon 1 is inserted in the right position in the body. At that time, the extruding force and the extruding direction can be adjusted very easily.

When the insertion of the absorbent material 2 into the body is over, the accommodating portion 3 can be withdrawn without a sense of unbelongingness because the accommodating portion 3 is withdrawn in a state where the accommodating portion is intimately attached with the index finger. Furthermore, when the index finger is withdrawn while holding the clamping plates 61, 61 with the other hand (see FIG. 10), the accommodating portion 3 surrounding the index finger is turned inside out and the dirty spot is not conspicuous. As the applicator is sanitary as it is, the applicator can directly be disposed in that state. Also, by using a water soluble film, the applicator can be flowed into water and therefore, the disposal becomes easier and convenient.

In the above-mentioned embodiment, only a tampon having the accommodating portion 3, which is gradually enlarged in diameter as it goes toward the framework 61, has been described. However, the present invention is not limited to this. For example, a tampon having the accommodating portion 3, which is enlarged in diameter and connected with the framework 61 like a flange may suffice the purpose with the same function and effect as that of the above-mentioned embodiment.

Also, a preferred embodiment of an applicator of the third invention, as shown in FIG. 5, comprises an accommodating portion 3 for accommodating therein an absorbent material 2, and a clamping portion 6 continuously connected with an opening portion of the accommodating portion 3, the accommodating portions 3 is formed of a flexible structure having an expansible property which can be enlarged in the radial direction, and the clamping portion 6 has a sufficient rigidity for holding the opening portion of the accommodating portion 3.

A flexible sheet as the flexible structure, which forms the applicator, has an anisotropic strong expanding property in which the strong expanding property in the vertical axial direction is different from the strong expanding property in the horizontal axial direction. The flexible sheet forms the accommodating portion 3 as such that the vertical axial direction, which is less expansible, is served as a longitudinal direction, while the horizontal axial direction, which is more expansible, is served as a radial direction.

The applicator of the third invention is formed of the fifth invention as will be described afterward.

As the most preferable flexible sheet for forming the accommodating portion 3, there is, for example, an unburned sheet of a tetrafluoroethylene resin. Also, as the most preferable flexible film or sheet, there is, for example, a blend film or sheet which is chiefly composed of low density polyethylene, or a composite thereof, or a film or sheet obtained by co-extruding an easy expansible resin and a non-easy expansible resin into a stripe shape through a molding machine or the like.

The unburned sheet of a tetrafluoroethylene resin used for forming the accommodating portion 3 is obtained by extruding or rolling an admixture of powder of polytetrafluoroethylene composed by a known polymerizing method such as, for example, a suspension polymerization or an emulsion polymerization, added with a suitable quantity of liquid lubricant.

The liquid lubricant used for the unburned sheet of a tetrafluoroethylene resin can wet the surface of polytetrafluoroethylene and it can be removed from the sheet by means of evaporation, extraction or the like at a decomposing temperature or less of polytetrafluoroethylene. As the liquid lubricant, there can be used, for example, a hydrocarbonic oil such as liquid paraffin, naphtha, white oil, etc., natural oil such as squalane, coconut oil, rapeseed oil, etc., aromatic hydrocarbon class such as toluene, xylene, decalin, etc., solvent such as alcohol class, ketone class, ester class, silicon oil, fluorochlorocarbonic oil, etc., solution of these solvents dissolved with a polymer such as polyisobutylene, polyisoprene, etc., a mixture of two or more of them, water or aqueous solution containing a surface-active agent, or the like.

As the low density polyethylene used for a blend film or a sheet chiefly composed of the low density polyethylene, there is, besides general-purpose low density polyethylene, linear-like low density polyethylene, and superlinear low density polyethylene. As an additive blended with the low density polyethylene, there is used one which has an effect for plasticizing the low density polyethylene, such as, for example, wax class such as polyethylene wax, etc., hydrocarbonic polymer having a side-chain such as atactic polypropylene, vaseline, liquid polybutadiene, liquid polybutene, terminal hydroxy liquid polybutadiene, liquid polyisoprene rubber, paraffin chloride, ethylene-propylene copolymer, hydrocarbonic polymer having a side-chain such as isobutylene polymer, etc., saturated or unsaturated natural or composite triglyceride, monoester, polyester of polybasic acid and monovalent alcohol, polyester of polybasic acid and polyvalent alcohol, or polyester (excluding triglyceride) of monobasic acid and polyvalent alcohol. Furthermore, there is polyester of polybasic acid and polyvalent alcohol, monobasic acid and/or monovalent alcohol having a carbon number of 6 to 22, for example, diester of gelbe alcohol and adipic acid, diester of gelbe alcohol having a carbon number of 20 to 24 and alkenyl succinic acid having a carbon number of 20 to 22, polyester of diethyleneglycol and dimer acid, polyester for partially or totally enclosing carboxylic acid or alcohol of both terminals of polyester of diethyleneglycol and dimer acid with stearic acid. As an additive having an effect for plasticizing these polyethylenes, there can be used an admixture of a single kind or two kinds or more. Furthermore, the low density polyethylene or blend film chiefly composed of the low density polyethylene can be used as a multi-layer composite film or sheet. As a method for making a film into a multi-layer structure, there is a known method such as coextrusion or lamination. As one which has so favorably adhesive property with respect to polyethylene as to be used for making the blend film or sheet chiefly composed of low density ethylene, there can be listed, for example, the blend films or the sheets themselves, ethylene-acetylvinyl copolymer, ethylene- α-olefin copolymer, propylene- α-olefin copolymer, etc. The multi-layer film is formed in a structure of two or more layers according to necessity. When a easy expanding resin and a non-easy expanding resin are used, they are coextruded into a stripe-shaped film or sheet by extrusion molding machine or the like.

As the easy expanding resin, there can be listed such a thermoplastic elastomer as, for example, a natural or synthetic rubber such as stylenebutadiene rubber, butadiene rubber, isoprene rubber, etc., a polystyrene group, a polyolefin group, a polyuretan group, polyester, a PVC group, a natural rubber group, aionomer, butyl rubber graft polyethylene, 1,2-polyethylene, trans, 1,4-polyisoprene, etc.

On the other hand, as the non-easy expanding resin, there can be listed, there is a crystalline giant molecule. As the giant molecule, there can be listed, for example, an olefin group such as polyethylene, polypropylene, etc., an amide group such as polyamide, etc., an acetal group such as polyacetal, etc., a vinyl group such as polyvinylidene chloride, a fluoride group such as polyethylenetetrafluoride, polyhexafluoropropyrene, an ester group such as linear polyester, etc.

In order to obtain an economic advantage, reduction of slide resistance, prevention of blocking, a filler may suitably be used for the flexible film or sheet for forming the accommodating portion. As the filler, one, which is inert and safe, is preferable. For example, there can be listed barium sulfate, calcium sulfate, burned gypsum powder, calcium carbonate, silica, titanium oxide, etc. They can be used by blending a single or several kinds of them.

The physical properties of the flexible film or sheet, which is used for the accommodating portion 3, are as follows. The maximum expanding strength in the radial direction of the accommodating portion 3 where the expanding property is large is 600 g/mm$^2$, the maximum expanding power is 200% or more, the tensile resilient force is 300 g/mm$^2$ or less, and more preferably, the maximum expanding strength is 300 g/mm$^2$, the expansible power is 500% or more, and the tensile resilient strength is 1500 g/mm$^2$. Furthermore, the maximum expanding ratio between the less expansible longitudinal (vertical axis) direction and the more expansible radial (horizontal axis) direction is $\frac{1}{3}$ or less, and more preferably 1/6 or less.

By establishing the maximum expanding strength, the maximum expanding power, the tensile resilient strength and the maximum expanding ratio in these ranges, the applicator, as the accommodation barrel 3, of the present invention, can easily be made of a sheet or film, although this was heretofore considered to be difficult.

As one, which exhibits difference in expanding property with respect to the longitudinal direction and the radial direction which is perpendicular to the longitudinal direction, there is the flexible fiber shaped structure besides the flexible film or sheet. As the flexible fibrous structure, there is a knit obtained by knitting fibers or net obtained by adhering fibers by means of welding or the like. As the knit, for example, plain knitting, milling knitting, pearl knitting, etc. are preferable, while as the net, one, which, when the accommodated absorbent material 2 is extruded, is expanded in the radial direction and spread in the fibers, is preferable. The knit or net can be used alone or as a composite with a sheet, a film or the like. The knit and net are formed by a method known per se. According to necessity, however, they may be formed by being cut away or being subjected to composite treatment and thereafter, sealed, adhered or sewn.

The physical properties of the knit or net, or composite of them which is used for the film or sheet of the accommodating portion 3, are as follows. The maximum expanding strength in the radial direction of the accommodation barrel where the expanding property is large until the accommodation barrel is expanded 100% is 100 g/mm or less, the maximum strength until the accommodation barrel is expanded 200% is 200 g/mm or less. Furthermore, the maximum expanding ratio between the less expansible longitudinal direction and the more expansible radial direction is $\frac{2}{3}$ or less, and more preferably, the maximum strength until the accommodation barrel is expanded 100% is 50 g/mm or less, and the maximum strength until the accommodation barrel is expanded 200% is 100 g/mm or less. Furthermore, the maximum expanding ratio between the less expansible longitudinal direction and more expansible radial direction is $\frac{1}{3}$ or less.

By establishing the maximum strength and the maximum expanding ratio in these ranges when the accommodation barrel is expanded 100% and 100% respectively, even in the case that the flexible structure is the fibrous structure, it can easily be expanded as an applicator of the present invention in the same manner as mentioned above.

Also, another preferred embodiment of the applicator of the third invention is constructed in accordance with the above-mentioned applicator. However, an unburned sheet of tetrafluoroethylene resin as a flexible structure forming an accommodating portion of an applicator of this embodiment has an expansion anisotropic property comprising a less expansible vertical axial direction (longitudinal direction of the accommodating portion 3) and a more expansible horizontal direction (radial direction of the accommodating portion 3). By using such unburned sheet of tetrafluoroethylene resin, the applicator of the present invention can be seamless molded by a method for manufacturing an applicator as will be described afterward.

Furthermore, the accommodating portion 3 may be one obtained by complexing the unburned sheet of tetrafluoroethylene resin by means of a known method such as lamination, coating or the like according to necessity. As one which is laminated, there are, for example, film, non-woven fabric, net, etc., while as one which is coated, there are, for example, metal, high molecule, activator, etc. These may be suitably arranged to improve the function according to purposes depending on the form and/or state of the outer surface and inner surface of the accommodating portion 3.

Figure 20:
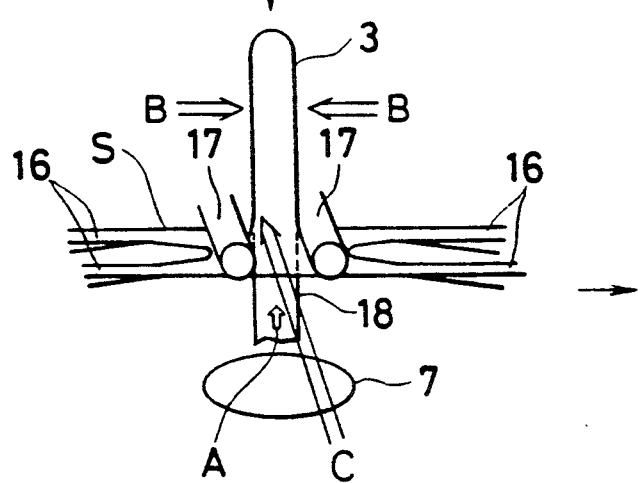

Also, the unburned sheet of tetrafluoroethylene resin, which is formed as the accommodating portion 3, is 70% or more, and more preferably 80% or more in degree of orientation of moles in the less expansible vertical axial direction (direction looked from the arrow B in FIG. 20, i.e., direction parallel to the longitudinal direction $S_1$ of the sheet S) when molding, while the unburned sheet is 50% or more, and more preferably 60% or more in degree of orientation of moles in the more expansible horizontal axial direction (direction looked from the arrow C in FIG. 20, i.e., direction $S_2$ perpendicular to the direction $S_1$). If the respective degrees of orientation of moles are not within the above-mentioned ranges, there is such a fear as that a satisfactory accommodating portion 3 is unobtainable both in respect of mechanical strength and function.

The above-mentioned degree of orientation of moles can be measured by such conventional method as X-ray analysis method, double refraction method, fluorescent deflection method, dielectric microwave method or the like. In the present invention, the degree of orientation was found with reference to a half value width of the peak value of an X-ray waveform using, for example, a method reported on an industrial chemical magazine vol. 39, p992 (1939) by Yukichi Kure and Kiichiro Kubo, or using the following relation (I) for finding the degree of orientation of moles written in "High molecule X-ray diffraction" (issued by Maruzen K. K.) p187 by Masao Sumido and Nobutami Kasai.

$$\text{degree of orientation } \pi = \frac{180° - H°}{180°} \times 100 \quad (I)$$

In the above relation, H° is a half value width of a strength distribution which is measured along the Debye-ring of diffraction which is the strongest on the equator.

The unburned sheet of tetrafluoroethylene resin is formed in the same manner as described in the fourth invention.

Next, the fourth invention will be described with reference to the preferred embodiment shown in FIGS. 11 through 17, wherein the same or similar parts of the embodiment of the third invention will be represented by the same reference numerals.

Figure 11:
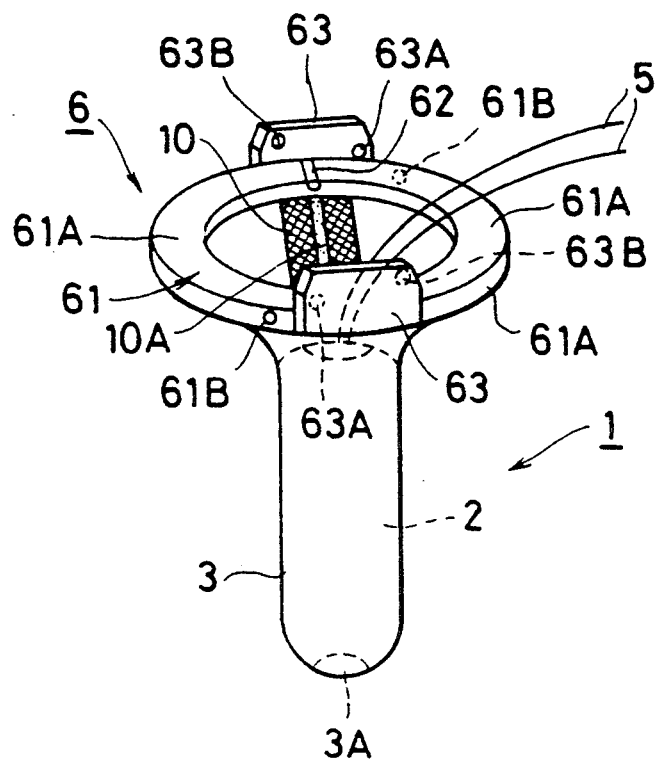
FIG. 11 is an overall perspective view showing one embodiment, in which the applicator of the fourth invention is applied to the tampon.

An applicator of this embodiment, as shown in FIG. 11, is constructed with reference to the applicator of the third and fourth invention and includes an accommodating portion 3 for accommodating therein an absorbent material 2, and a clamping portion 6 continuously connected to an opening portion of the accommodating portion 3, the accommodating portion 3 is formed of a flexible structure which has an expanding property able to be expanded in the radial direction, and the clamping portion 6 has a sufficient rigidity for holding the opening portion of the accommodating portion 3.

And, a sheet S used as the flexible structure of this embodiment is provided at least at a part of an inner surface thereof with substantial irregularities. As the sheet S has substantial irregularities, in the case that the sheet S forms the inner surface of the accommodating portion 3, intimacy (frictional force) between the inner surface and the finger is reduced to enhance a smooth insertion of the absorbent material 2 accommodated in the accommodating portion 3 into the body. The irregularities are obtained by integrally forming a net 10 on the outer surface of the sheet S by suitable means such as heating or the like.

In this embodiment, an unburned sheet of tetrafluoroethylene resin (PTFE) is used as the sheet S. The sheet S is formed as a flat and smooth surface. The outer surface of the sheet S, as shown in FIGS. 13 through 15, is provided with a polyethylene net 10 having a width narrower than that of the sheet S and superposed on the outer surface of the sheet S. In the foregoing state, the net 10 is jointed to the outer surface of the sheet S in the longitudinal direction by heating and integrally formed by a heat jointing portion 10A. Also, it can be designed as such that the net 10 is formed into a narrow shape in the vicinity of its center in the longitudinal direction, so that it would be subjected to seamless treatment by a method for manufacturing an applicator as will be described afterward. Also, the remaining part of the net 10 excluding the heat jointing portion 10A, as shown in a sectional view of FIG. 14, is free. Therefore, in the case that the inner surface of the accommodating portion 3 is formed, the accommodating portion 3 can easily be subjected to expansion molding without being interfered by the net 10. The net 10 may be welded to a straight barrel portion within the inner surface of the accommodating portion 3, and preferably to a portion more than 10 cm from the lower end but upto the starting edge of the enlarging diameter of its upper portion.

As the most preferable flexible sheet S for forming the accommodating portion 3, there can be listed the above-mentioned unburned sheet of an ethylene tetrafluoride resin, a blend sheet which is chiefly composed of low density polyethylene, or a composite thereof, or a sheet obtained by co-extruding an easy expansible resin and a non-easy expansible resin into a stripe shape through a molding machine or the like.

In this embodiment, the absorbent material 2 is formed of the same material as that of the conventional one, and the physical properties of the PTE unburned sheet are, for example, as follows.

① The tensile strength in the MD direction of the film is 1200 g/mm$^2$ and the expanding power is 200%.

② The tensile strength in the TD direction (horizontal direction) of the film is 100 g/mm$^2$ and the expanding power is 800%.

Also, as the net, there is one as listed hereunder.

① The weighing quantity is 20 g/m$^2$.

② The horizontal strength is 200 g/15 mm width.

Figure 19:
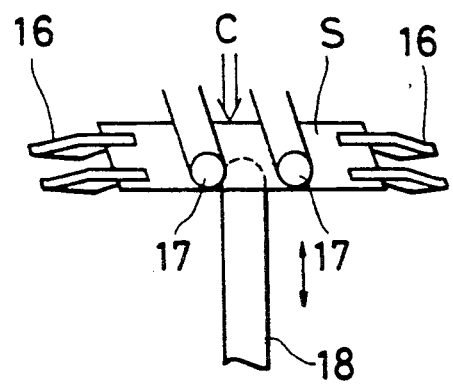
Figure 22:
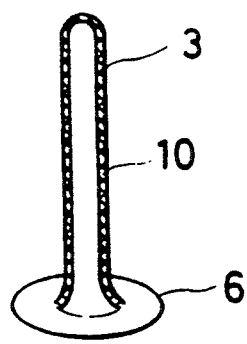

This laminated sheet S was pressed at its portion which was not desired to be expanded by means of an expanding device of FIGS. 19 and 20, and the remaining portion which was desired to be expanded was left free. In the foregoing state, the sheet S was subjected to seamless molding. As a result, it was found that a part of the sheet S was expanded and the remaining part thereof was contracted, and finally it formed the accommodating portion 3 of an applicator which can be expanded in the radial direction as shown in FIG. 22.

A tampon using the applicator 1 of the present invention, like the embodiment of FIG. 11, is constructed in the substantially same manner as the embodiment of the applicator of the third invention excepting that the tampon of this embodiment has substantial irregularities at least at a part of its inner surface. In this embodiment, therefore, the connecting state between the accommodating portion 3 and the clamping portion 6 will be described.

Figure 12:
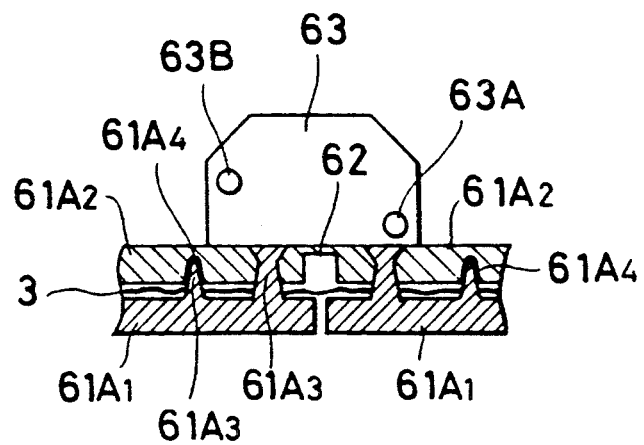
FIG. 12 is an enlarged sectional view of a clamping portion thereof.

Also, the framework element 61A, as shown in FIG. 12, comprises semicircular framework element members 61A$_1$ and 61A$_2$ superposed one upon the other. And, the lower framework element member 61A$_1$ is formed with a plurality of knob portions 61A$_3$ at predetermined spaces in the circumferential direction, while the upper framework element member 61A$_2$ is formed with a plurality of recessed portions 61A$_4$ at predetermined spaces in the circumferential direction. In FIG. 12, the knob portions 61A$_3$ are in engagement with the recessed portions 61A$_4$ and the upper and lower framework element members 61A$_1$ and 61A$_2$ are superposed one upon the other with the edge of the enlarged diameter portion of the accommodation barrel 3 sandwiched therebetween. The lower framework element member 61A$_1$ and the upper framework element member 61A$_2$ are connected with each other by a hinge (not shown) similar to the hinge 62 for interconnecting the framework elements 61A, 61A. When the superposing state of them is removed, the lower framework element members 61A$_1$, 61A$_1$ form a circular-shape, and the upper framework element members 61A$_2$, 61A$_2$ are integrally developed at both sides of the circle through the aforementioned hinge (not shown).

Also, the accommodating portion 3 is provided with a hole 3A having a diameter which is gradually reduced as it goes toward the tip. This hole 3A is dilated when the absorbent material 2 of the tampon 1 is pushed away from the accommodating portion 3.

A method for manufacturing an applicator of the fifth invention will be described next. The method of this invention is suitably used when the applicator used in the tampon of the first and second invention and the applicator of the third and fourth invention.

One mode of the method of the present invention will be described on the case where an applicator of a tampon is manufactured with reference to FIGS. 18 through 25.

Figure 18:
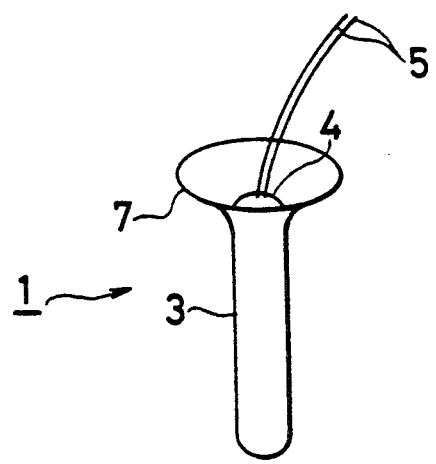
FIG. 18 is a perspective view showing a tampon formed of an applicator which is manufactured according to a method for manufacturing an applicator of the fifth invention.

The applicator used in the tampon 1 which is manufactured according to the mode of this embodiment includes an accommodating portion 3 and a ring 7 continuously connected with the accommodating portion 3 as shown in FIG. 18. And, if the applicator accommodates therein the absorbent material 2 for example, it forms a tampon. In FIG. 18, 5 is a string for withdrawing the absorbent material 2 from the inserted position.

Now, a sheet S used for manufacturing the accommodating portion 3 is not substantially expanded in the vertical axial direction but is expansible in the horizontal axial direction. That is, the sheet S, when plastically deformed by means of an expanding operation, is hardly expanded because the expansion stress in the vertical axial direction is within a range of its resiliency owing to its large tensile strength in the vertical axial direction. On the contrary, as the tensile force in the horizontal direction is small, the expanding stress in the horizontal axial direction exceeds the range of its resiliency and the sheet S is mostly expanded in this direction. In other words, a uniaxial expansion occurs. As a result, the accommodating portion 2 is formed.

In the case that the accommodating portion 3 is manufactured using the sheet S, a manufacturing apparatus as shown for example in FIGS. 19 and 20 is employed. The manufacturing apparatus comprises a fixing device 16 for fixing the sheet S at its four spots at the substantially corner portions, a pair of pressing members 17, 17 which are disposed in such a manner as to intersect at right angles with the longitudinal direction of the sheet S in order to press the upper surface of the sheet S, and a rod-like molding member 18 which is disposed between the pressing members 17, 17 and adapted to apply a concentrated load onto the sheet S while advancing upward between the pressing members 17, 17 from the lower surface of the sheet S in order to expand the sheet S as shown in FIG. 19.

Figure 21:
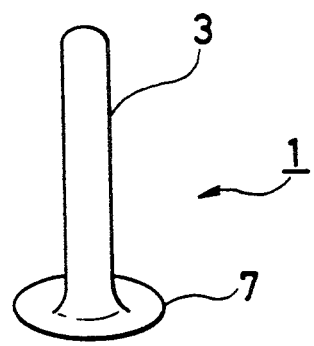
FIGS. 21 and 22 are perspective views respectively showing an applicator wherein an accommodating portion is attached with a ring.

Therefore, when the sheet S is fixed at said four substantially corner portions, if the molding member 18 is advanced upward (the direction as shown by the arrow A in FIG. 20) to apply a concentrated load to between the pressing members 17, 17 more precisely, to the center with respect to said four substantially corner portions, the molding member 18 covered with the sheet S is advanced upward. At this time, the sheet S is expanded and plastically deformed to form the accommodating portion 3. After the sheet S is formed into the accommodating portion 3, the ring 7 is attached to the root portion of the accommodating portion 3 and the remaining sheet S is treated. As a result, there can be obtained an applicator as shown in FIG. 21.

The expanding process of the sheet S during the above-mentioned expanding operation will be described by way of analytical method with reference to FIGS. 23 through 26.

Figure 23:
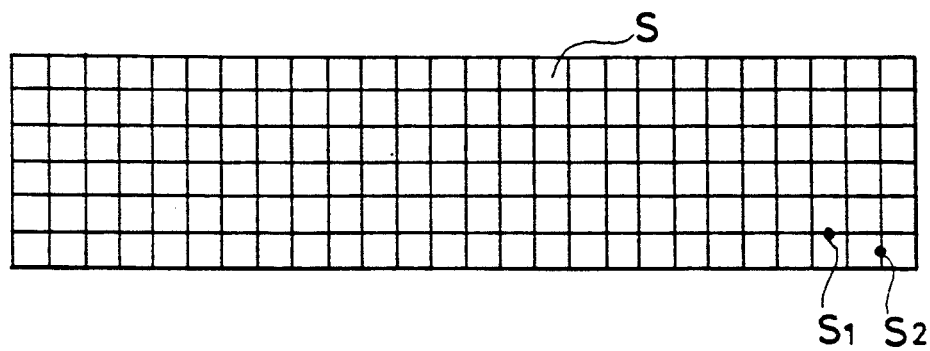
Figure 24:
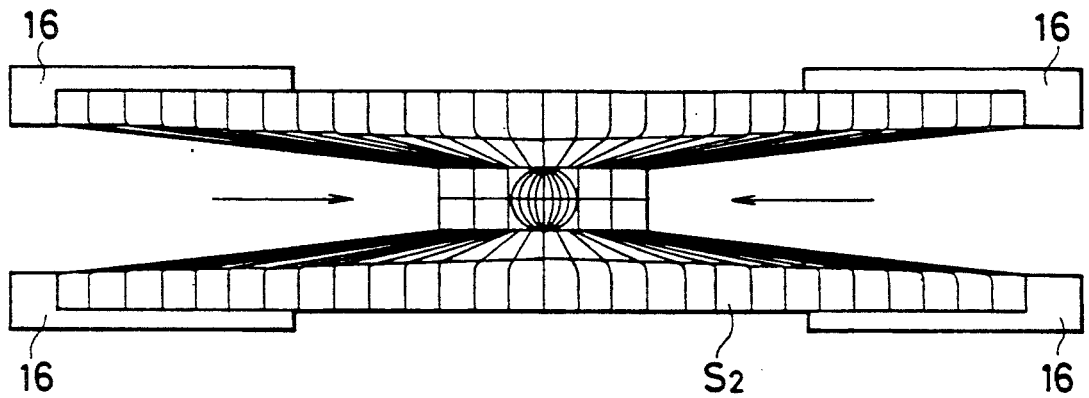
Figures 25, 26:
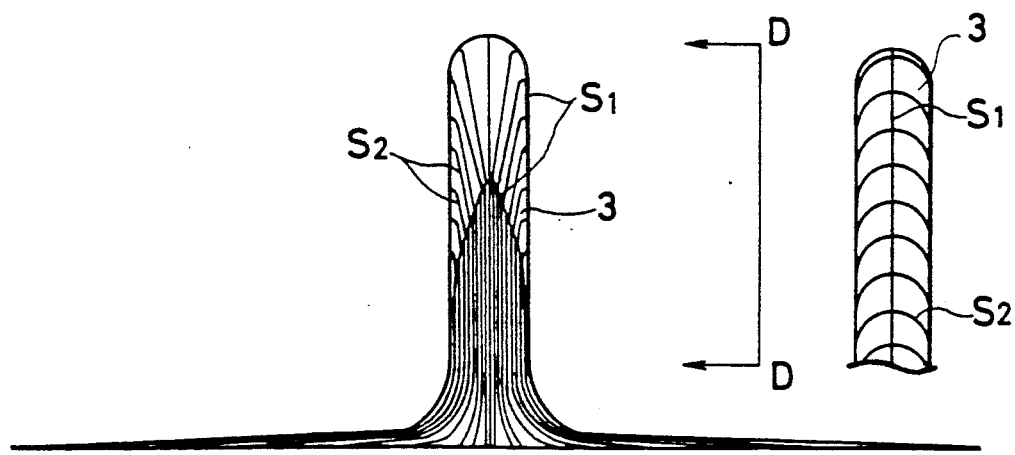

That is, in order to analytically review the change of the various portions of the sheet S when the sheet S is being expanded, as shown in FIG. 23, a mesh of 5 mm is imaginarily formed by means of vertical lines $S_1$ and horizontal line $S_2$ and the above-mentioned concentrated load is applied to the sheet S which is formed with the mesh. As a result, as shown in FIG. 24, a portion of the sheet S corresponding to a width of 5 mm at the edges of both sides thereof in the longitudinal direction is hardly expanded and remained unchanged. A mesh portion corresponding to a four row portion in the longitudinal direction at the inner sides of them is progressed inwardly as shown by the arrow of FIG. 24 to form the accommodating portion 3 as shown in FIG. 24. At this time, as the sheet S has a large tensile force in the vertical axial direction, i.e., in the longitudinal direction, the sheet S is hardly expanded in that direction. On the other hand, as the tensile force is small in the horizontal axial direction, the sheet S receives an expanding function in that direction and is expanded. Therefore, the vertical line $S_1$ at the accommodating portion 3 is not changed in dimension. On the contrary, the horizontal line $S_2$ is greatly expanded as shown in FIG. 25.

The above-mentioned expanding function will be described more concretely on a case where a polytetrafluoroethylene raw sheet is used.

The polytetrafluoroethylene raw sheet is obtained as follows. Unburned polytetrafluoroethylene powder is added with a suitable quantity of liquid lubricant to make an admixture. The admixture is formed into an elongated sheet by suitable means including at least an extruding method or a rolling method. Thereafter, the elongated sheet is dried at a temperature of 200° C. or less. Such obtained polytetrafluoroethylene raw sheet was made into a barrel-like goods 2 under the following conditions.

(I) Conditions
①  sheet size: 130 mm(L)×40 mm(W)×60μ (T)
②  molding member: rod of 10 mm($\phi$)
③  concentrated load: 1 kg (II) Obtained barrel-like goods
①  size:
    length (L)=60 mm
    diameter (D)=10 mm
    L/D=6
②  enlarged diameter in radial direction=10 mm(D)→30 mm(D)
③  enlarged load in back direction: 500 g
    (when finger is inserted)

The polytetrafluoroethylene raw sheet was found to be expanded eight times in the horizontal axial direction.

As described in the foregoing, according to the above-mentioned embodiment, as apparent from the above-mentioned result, there could be obtained an applicator having a thickness of 60μ and an L/D of 6, which was expected to be obtainable according to the prior art.

If the applicator including the accommodating portion 3 according to the method of the present invention is applied to a tampon, the following advantages are obtainable.

That is, the above-mentioned applicator is thinner and smaller in diameter compared with the conventional applicator, and it has a flexible film-like shape. Therefore, the applicator is easy to insert as a tampon.

While the conventional applicator is a two-piece construction comprising an outer barrel and an inner barrel, the above-mentioned applicator is a one-piece construction, short in length and generally similar to the absorbent material. Accordingly, it can be held in one hand as a tampon.

Furthermore, when in use, the ring 7 is held in one hand and inserted into the body. Then, the absorbent material 4 is inserted into the body with the index finger. Thereafter when the index finger is withdrawn, the applicator fits well to the index finger and comes out together with the finger because the applicator is like a film. When the applicator has been withdrawn, the ring 7 is held by other finger and the index finger is pulled out. As a result, the applicator is turned inside out thus bringing the dirty outer surface thereof inside. Therefore, the applicator can be disposed as it is without worrying about its sanitarium.

TEST EXAMPLE

Next, the third invention will be described more concretely with reference to test examples. The absorbent material 2 used in the test examples and comparison examples was 54 mm in length and 11.5 mm in diameter. An opening portion having a diameter of 8 mm was formed in the tip of the accommodating portion 3. The accommodating portion 3 was 60 mm in length from the framework 6 to the tip.

Test examples and comparison examples of the third invention will be described first.

In this test example, a sheet having an expansion anisotropic property and a fibrous structure having an anisotropic expansion were used, and they were subjected to seamless treatment and heat seal treatment. As a result, an accommodating portion 3 of the applicator 1, which can be enlarged in the radial direction, was obtained.

In this way, as the accommodating portion 3 was constructed as such that the accommodating portion 3 was enlargeable in the radial direction, the outer diameter of the applicator 1 could be made so small as to be very close to the outer diameter of the absorbent material 2. As a result, the inserting resistance could be made small.

TEST EXAMPLE 1

An unburned sheet of tetrafluoroethylene resin (thickness of $60\mu$) was subjected to seamless treatment by holding the longitudinal direction of the film using an apparatus shown in FIGS. 19 and 20. Such obtained film was made into the accommodating portion 3. And, a tampon 1 including the accommodating portion 3 was prepared.

Then, a strip-shaped test sample was cut out from the central portion of the accommodating portion 3, and a test sample having a length of 10 mm and a width of 10 mm was prepared. Such obtained test sample was subjected to a tension test at a pull speed of 200 mm/min. Also, the elastic modulus of tension was found from the inclination of a tangent line till the strong expansion curve was expanded 5%, and the sectional area of the test sample at the time when strength was measured was found by dividing the original sectional area.

TEST EXAMPLE 2

An accommodating portion 3 was formed from an unburned sheet of tetrafluoroethylene resin (thickness of $60\mu$) by serving the longitudinal direction of the sheet as the longitudinal direction of the accommodating portion 3 and an applicator was prepared as shown in FIG. 21. A test sample was prepared in the same manner as the test example 1, and the physical properties of this test sample was measured in the same procedure as the test example 1.

TEST EXAMPLE 3

A plasticized film (manufactured by Fuji Photo Film Co., Inc., Merchandise Name: Sealon Film, thickness of $130\mu$) plasticized by adding an additive chiefly containing a paraffin oil to a low density polyethylene was prepared in the same procedure as the test example 1. Then, a test sample was prepared and the physical properties of such prepared test sample were measured in the same manner as the test example 1.

TEST EXAMPLE 4

A plasticized film (manufactured by Fuji Photo Film Co., Inc., Merchandise Name: Sealon Film, thickness of $130\mu$) plasticized by adding an additive chiefly containing a paraffin oil to a low density polyethylene was expanded four times in the uniaxial direction, and heat sealed to form an accommodating portion 3 by serving its expanding direction as the longitudinal direction of the accommodating portion 3. In this way, an applicator of FIG. 21 was prepared. Then, a test sample was prepared in the same manner as the test example 1. The physical properties of such prepared test sample were measured by the same procedure as the test example 1.

TEST EXAMPLE 5

100 wt. parts of a low density polyethylene was added with 10 wt. parts of a liquid rubber and 150 wt. parts of a filler. After kneaded by a kneading machine, the resultant was pressed at 120° C. into a sheet. Then, the sheet was molded in the same manner as the test example 1. As a result, an applicator of FIG. 21 was prepared. Then, a test sample was prepared in the same manner as the test example 1. The physical properties of such prepared test sample were measured in the same procedure as the test example 1.

TEST EXAMPLE 6

The press sheet obtained in the test example 5 was expanded six times in the uniaxial direction and then, heat sealed to form an accommodating portion 3 by serving the expanding direction as the longitudinal direction of the accommodating portion 3. In this way, an applicator 1 of FIG. 21 was prepared. Then, a test sample was prepared in the same manner as the test example 1. The physical properties of such prepared test sample were measured in the same procedure as the test example 1.

TEST EXAMPLE 7

A low density polyethylene and a stylene-ethylene-butadiene-stylene copolymer were coextruded into a stripe-shape and then, heat sealed to form an accommodating portion by serving the longitudinal direction of this film (thickness of $80\mu$) as the longitudinal direction of the accommodating portion 3. In this way, a tampon of FIG. 21 was prepared. Then, a test sample was prepared in the same manner as the test example 1. The physical properties of such prepared test sample were measured in the same procedure as the test example 1.

COMPARISON EXAMPLE 1

A low density polyethylene (thickness of $60\mu$), which was pressed at 120° C., was subjected to seamless treatment at 100° C. using an apparatus as shown in FIGS. 19 and 20. Such treated film was made into an accommodating portion 3, and in this way, an applicator 1 of FIG. 21 was prepared. Then, the physical properties thereof were measured in the same procedure as the test example 1.

COMPARISON EXAMPLE 2

A natural rubber sheet (thickness of 130μ) was heat sealed to form an accommodating portion 3 by serving the longitudinal direction of this sheet as the longitudinal direction of the accommodating portion 3, and in this way, an applicator 1 of FIG. 21 was prepared. And, the physical properties of a test sample thereof were measured in the same procedure as the test example 1.

TEST EXAMPLE 8

In this test example, a net was used. The net (manufactured by Mitsui Sekiyu Kagaku K.K., merchandise name: Netron) was obtained by heat fusing a space between adjacent fibers. The net was heat sealed to form an accommodating portion 3 by serving the less expansible longitudinal direction as the longitudinal direction of the accommodating portion 3, and in this way, an applicator 1 of FIG. 21 was prepared. Then, a strip-shaped test sample was cut out from the central portion of the accommodating portion 3, and a test sample having a length of 20 mm and a width of 10 mm was prepared. Such obtained test sample was subjected to a tension test at a pull speed of 200 mm/min.

TEST EXAMPLE 9

In this test example, a knit was used. The knit was obtained by knitting nylon fibers of 10 deniers into a barrel-shape by means of plain knitting, and a tampon 1 of FIG. 21 was prepared by serving the longitudinal direction of the knit as the longitudinal direction of the accommodating portion 3. A tension test, etc. were carried out in the same manner as the test example 8.

TEST EXAMPLE 10

In this test example, a net was used. The net (manufactured by Mitsui Sekiyu Kagaku Kogyo K.K., Merchandise Name: Netron) was obtained by heat fusing a space between the adjacent fibers. Furthermore, a composite sheet was prepared from this net by heat fusing a film of stylene-ethylene-butadiene-stylene copolymer (thickness of 60μ) between rolling rolls. An accommodating portion 3 was formed by serving the longitudinal direction of this composite sheet as the longitudinal direction of the accommodating portion 3, and in this way, an applicator of FIG. 21 was prepared. And, a tension test, etc. were carried out in the same manner as the test example 8.

Furthermore, in addition to the above-mentioned various tests, evaluation was carried out on the function of the accommodating portions 3 of the applicators 3 prepared in the above-mentioned various tests whether function as an accommodating portion 3 was satisfied. Evaluated results were as follows.

That is, function evaluation at the time when the absorbent material 2 was pushed away from the accommodating portion 3 with the index finger of an average woman having a length of 80 mm and a circumference of 55 mm was carried out as follows.

Smoothly pushed away without any resistance . . . ⊚

Accommodating portion 3 and clamping portion 6 were pushed away with some resistance but without being broken . . . ○

There was resistance and accommodating portion 3 and clamping portion 6 were partly broken, but they were somehow pushed away . . . △

There was resistance and expansion in the longitudinal direction, and thus unable to push away . . . X According to the test results of the above-mentioned various test examples and comparison examples which are shown in table 1, table 2, and table 3, the following things are made apparent.

According to table 1 showing the results of the test examples 1 through 7, the maximum expanding strength and tension elastic modulus in the radial direction of the accommodating portions 3 of the test examples 1 through 7 are significantly small when compared with the applicators of the comparison examples 1 and 2, and the maximum expanding power in the radial direction of the accommodating portions 3 is small. Therefore, there can be made small the accommodating portion 3 for containing the absorbent material 2. Therefore, after the absorbent material 2 is set in the body, the accommodating barrel 3 can be pulled out in such a manner as that the finger is wound around by the accommodation barrel 3. Then, the accommodating portion 3 can easily be detached from the finger, and the applicator can be folded into a small size and disposed. Any of the applicators of the test examples 1 through 7 is excellent in function as the accommodating portion 3.

Also, according to table 3 showing the results of the test examples 8 and 9, there is no great difference in maximum strength when the accommodating portion 3 is expanded 100% and when it is expanded 200%. Therefore, the absorbent material 2 or the finger is not excessively fastened by the accommodating portion 3. Therefore, it exhibits an excellent function as an accommodating portion 3.

Next, other test examples and comparison examples of the third invention will be described more concretely.

The absorbent material 2 used in the test examples and comparison examples was 54 mm in length and 11.5 mm in diameter. An opening portion having a diameter of 8 mm was formed in the tip of the accommodating portion 3. The accommodation barrel 3 was 60 mm in length from the framework 6 to the tip.

In this way, as the accommodating portion 3 was constructed as such that the accommodating portion 3 was enlargeable in the radial direction, the outer diameter of the tampon 1 could be made so small as to be very close to the outer diameter of the absorbent material 2. As a result, the inserting resistance could be made small.

TEST EXAMPLE 11

In this test example, an unburned sheet of tetrafluoroethylene resin (thickness of 60μ), which was 85 % in degree of orientation of moles π, was subjected to seamless treatment to form an accommodating portion 3 by holding an end portion of the longitudinal direction of the unburned sheet of tetrafluoroethylene resin using an expanding apparatus of FIGS. 19 and 20. In this way, an applicator 1 of FIG. 21 was prepared. The molding of the accommodating portion 3 was carried out in a thermostatic chamber of 25° C.

Then, a strip-shaped test sample was cut out from the central portion of the accommodating portion 3, and a test sample having a length of 25 mm and a width of 5 mm was prepared. As shown in FIG. 20, four test samples were cut out from the surfaces B,B and C,C of one accommodating portion 3. Then, such pairs of surfaces B,B and C,C are folded into two at the centers thereof by paying a special attention so that the expanding axes would not be displaced between the test samples, and these test samples were used for X-ray measurement. In the X-ray measurement, Cu-Kα ray filtrated through a nickel filter was used and a clear peak where two θ (θ is a Bragg angle) appear in the vicinity of 18° in the direction of the equator was used. Measurement of X-ray diffraction was carried out in accordance with the conventional method (for example, art of fiber and high molecule measuring method (p167), edited by Fiber Academy, Asakura Shoten), and the mole degree of orientation π was found using the afore-mentioned relation (I). The measurement was carried out at 25° C.

TEST EXAMPLE 12

In this test example, an unburned sheet of tetrafluoroethylene resin (thickness of 60μ), which was 70% in degree of orientation of moles π, was subjected to seamless treatment to form an accommodating portion under the same conditions and by the same apparatus as the test example 11, and an applicator 1 of FIG. 21 was prepared. With respect to such prepared test sample, a mole degree of orientation π was found in the same manner as the test example 11.

COMPARISON EXAMPLE 3

In this comparison example, an unburned sheet of tetrafluoroethylene resin (thickness of 60μ), which was 40% in degree of orientation of moles π, was subjected to seamless treatment to form an accommodating portion under the same conditions and by the same apparatus as the test example 11, and an applicator 1 of FIG. 21 was prepared. With respect to such prepared test sample, a mole degree of orientation π was found in the same manner as the test example 11.

COMPARISON EXAMPLE 4

In this comparison example, an unburned sheet of tetrafluoroethylene resin (thickness of 60μ) having no degree of orientation of moles was subjected to seamless treatment under the same conditions and by the same apparatus as the test example 11. The sheet having no degree of orientation of moles is formed by stacking up a plurality of sheets used in the test example 11 in random directions and rolling the same into an accommodating portion 3. In this way, an applicator 1 of FIG. 21 was prepared. Then, with respect to such prepared test sample, a mole degree of orientation π was found in the same manner as the test example 11.

Further, evaluation was carried out on the function of the accommodating portions 3 of the tampons 1 prepared in the above-mentioned test examples 11 and 12 and comparison examples 3 and 4 whether function as an accommodating portion 3 was satisfied. The evaluation was carried out as follows, and the evaluated results were shown in table 4 and table 5.

That is, function evaluation at the time when the absorbent material 2 was pushed away from the accommodating portion 3 with the index finger on an average woman having a finger length of 80 mm and a circumference of 55 mm was carried out as follows.
Able to smoothly push away . . . ⊚
Able to smoothly push away from the accommodating portion 3 although it was slightly expanded in the elongated direction . . . ○
Unable to completely push away from the accommodating portion 3 because it was expanded in the longitudinal direction . . . Δ
Unable to push away because it was expanded in the lopngitudinal direction . . . X The applicator, which satisfies the conditions of the test examples 11 and 12, satisfies the function as an accommodating portion 3. Therefore, after the absorbent material 2 is set in the body, the accommodating barrel 3 can be pulled out in such a manner as that the finger is wound around by the accommodation barrel 3. Then, the accommodating portion 3 can easily be detached from the finger, and the applicator can be folded into a small size and disposed.

That is, according to the results of test examples 11 and 12 shown in table 4. it is known that if the degree of orientation of moles is 70% or more at the first part which gives an influence to the expansion in the elongated direction of the applicator and if the degree of orientation of moles, which gives an influence to the expansion in the radial direction of the applicator, is 50% or more, it satisfies the function as an applicator.

Also, according to the results of test examples 3 and 4 of table 5,1 the following facts are known. In the case that the degree of orientation of moles of a plane having a high degree of orientation of moles after molding of the applicator is 70% or less, the accommodating portion 3 tends to expand in the vertical direction when an absorbent goods, medical products, etc. accommodated in the accommodating portion 3 are inserted into the body. As a result, the absorbent goods, medical products, etc. are not smoothly pushed away into the body. On the other hand, in the case that the degree of orientation of moles of a plane having a low degree of orientation of moles is 50% or less, the accommodating portion 3 is difficult to expand in the horizontal direction when inserted into the body. As a result, it is difficult to smoothly push away the absorbent goods, medical products, etc. into the body.

In addition, in the explanation of the above-mentioned test examples, comparison examples 1 and 2 are comparison test examples in contrast with test examples 1 through 9, as well as test examples 3 and 4 are comparison test examples in contrast with test examples 11 and 12.

TABLE 1

| Test Example No. | Maximum expanding strength in radial direction of accommodating barrel g/mm² | Maximum expanding power in radial direction of accommodating barrel % | Tension elastic modulus g/mm² | Maximum expanding ratio between elongated and radial directions of accommodating barrel | Satisfaction of function as accommodating barrel |
|---|---|---|---|---|---|
| 1 | 120 | 725 | 230 | 1/16 | ⊚ |
| 2 | 120 | 740 | 1385 | 1/12 | ⊚ |
| 3 | 340 | 626 | 1270 | 1/12 | ○ |
| 4 | 410 | 403 | 1020 | 1/20 | ○ |
| 5 | 470 | 520 | 2700 | 1/6 | Δ |
| 6 | 430 | 470 | 2440 | 1/6 | Δ |
| 7 | 550 | 250 | 1760 | 1/8 | ○ |

TABLE 2

| Comparison example No. | Maximum expanding strength in radial direction of accommodating barrel g/mm² | Maximum expanding power in radial direction of accommodating barrel % | Tension elastic modulus g/mm² | Maximum expanding ratio between elongated and radial directions of accommodating barrel | Satisfaction of function as accommodating barrel |
|---|---|---|---|---|---|
| 1 | 1000 | 150 | 6000 | 1/4 | × |
| 2 | 150 | 1290 | 1710 | 1/1 | × |

TABLE 3

| Test Example No. | Maximum strength until 100% expantion in radial direction of accommodating barrel g/mm | Maximum strength until 200% expantion in radial direction of accommodating barrel g/mm | Maximum expanding ratio between elongated and radial directions of accommodating barrel | Satisfaction of function accommodating barrel |
|---|---|---|---|---|
| 8 | 10 | 17 | 1/2 | ⊚ |
| 9 | 3 | 46 | 2/3 | ○ |
| 10 | 40 | 60 | 3/5 | ○ |

TABLE 4

| Test Example No. | Degree of orientation of mole before molding applicator % | Degree of orientation of mole in direction A after molding applicator % | Degree of orientation of mole in direction B after molding applicator % | Satisfaction of function as accommodation barrel |
|---|---|---|---|---|
| 11 | 85 | 82 | 60 | ⊚ |
| 12 | 70 | 65 | 50 | ○ |

TABLE 5

| Comparison Example No. | Degree of orientation of mole before molding applicator % | Degree of orientation of mole in direction A after molding applicator % | Degree of orientation of mole in direction B after molding applicator % | Satisfaction of function as accommodation barrel |
|---|---|---|---|---|
| 3 | 40 | 43 | 40 | × |
| 4 | 0 | 45 | 45 | △ |

What is claimed is:

1. A tampon, comprising an absorbent material and an accommodation barrel for accommodating said absorbent material therein, said accommodation barrel containing an opening portion at one end and a closing portion at the other, and including an absorbent material accommodating portion for accommodating therein said absorbent material and a clamping portion continuously connected with the open portion of said absorbent material accommodating portion, said absorbent material accommodating portion being formed of a flexible structure which has an expanding property such that it can expand in the radial direction, wherein said flexible structure is formed of a sheet or a fibrous structure possessing a strong anisotropic expanding property wherein said property is different in the directions of the vertical and horizontal axes, respectively, said accommodating portion being formed of said flexible structure such that the less expanding vertical axial direction of the flexible structure serves as the longitudinal direction, while the more expanding horizontal axial direction thereof serves as the radial direction, said clamping portion being formed as a large diameter portion which is provided with a ring on an outer circumferential edge thereof, the sheet is 600 g/mm² or less in maximum expanding strength in the horizontal axial direction, 200% or more in maximum expanding power in the horizontal direction, and 3000 g/mm² or less in tension elastic strength, the maximum expanding ratio between the vertical and horizontal axial directions being ⅓ or less.

2. The tampon of claim 1, wherein said clamping portion is formed from a plurality of framework elements which are adapted to form a framework, and which are foldable.

3. The tampon of claim 1, wherein said clamping portion is formed of a framework having sufficient rigidity for holdiang said opening portion of said accommodating portion.

4. A tampon, comprising an absorbent material and an accommodation barrel for accommodating said absorbent material therein, said accommodation barrel containing an opening portion at one end and a closing portion at the other, and including an absorbent material accommodating portion for accommodating therein said absorbent material and a clamping portion continuously connected with the open portion of said absorbent material accommodating portion, said absorbent material accommodating portion being formed of a flexible structure which has an expanding property such that it can expand in the radial direction, wherein said flexible structure is formed of a sheet or a fibrous structure possessing a strong anisotropic expanding property wherein said property is different in the direction of the vertical and horizontal axes, respectively, said accommodating portion being formed of said flexible structure such that the less expanding vertical axial direction of the flexible structure serves as the longitudinal direction, while the more expanding horizontal axial direction thereof serves as the radial direction, said clamping portion being formed as a large diameter portion which is provided with a ring on an outer circumferential edge thereof, said flexible structure being formed from an unburned sheet to tetrafluoroethylene resin of an anisotropic strong expanding property which has a different strong expanding property in the vertical and horizontal axial directions respectively, said accommodating portion being seamless molded of said unburned sheet of a tetrafluoroethylene resin such that the less expanding vertical axial direction of said unburned sheet serves as the longitudinal direction, while the more expanding horizontal axial direction thereof serves as the radial direction.

5. The tampon of claim 4, wherein the degree of orientation of mole in the vertical axial direction is 70% or more, and the degree of orientation of mole in the horizontal direction is 50% or more.

6. The tampon of claim 4, wherein said clamping portion is formed from a plurality of framework elements which are adapted to form a framework, and which are foldable.

7. The tampon of claim 4, wherein said clamping portion is formed of a framework having sufficient rigidity for holding said opening portion of said accommodating portion.

* * * * *